US006130091A

United States Patent [19]
Binz et al.

[11] Patent Number: 6,130,091
[45] Date of Patent: Oct. 10, 2000

[54] METHOD FOR OBTAINING A PEPTIDE DERIVED FROM THE RESPIRATORY SYNCYTIAL VIRUS POLYPEPTIDE AND BACTERIUM EXPRESSING IT

[76] Inventors: Hans Binz, Les Crêtes, 74160 Beaumont; Thien Nguyen Ngoc, 7 les Petits Hutins Lathoy, 74160 St Julien En Genevois, both of France; Stefan Stahl, Torphagsvägen 8; Mathias Uhlen, Surbrunnsgatan 7, both of S-104 05 Stockholm, Sweden; Per Ake Nygren, Pilotgatan 22, S-128 32 Skarpnack, Sweden

[21] Appl. No.: 08/836,504

[22] PCT Filed: Nov. 7, 1995

[86] PCT No.: PCT/FR95/01465

§ 371 Date: Jul. 1, 1997

§ 102(e) Date: Jul. 1, 1997

[87] PCT Pub. No.: WO96/14418

PCT Pub. Date: May 17, 1996

[30] Foreign Application Priority Data

Nov. 7, 1994 [FR] France .................................... 94 13309

[51] Int. Cl.⁷ .............................. C12N 7/00; C12N 1/00; C12N 15/00; A61K 39/155
[52] U.S. Cl. ...................... 435/470; 435/476; 435/252.3; 435/882; 424/200.1; 424/211.1; 530/350; 530/300
[58] Field of Search .............................. 424/199.1, 200.1, 424/204.1, 211.1, 187.1, 185.1; 435/252.3, 822, 235.1, 470, 320.1, 476; 536/23.72; 530/350, 300, 387.1

[56] References Cited

FOREIGN PATENT DOCUMENTS

WO 87 04185  7/1987  WIPO .
WO 89 02935  4/1989  WIPO .
WO 92 20805  11/1992  WIPO .

OTHER PUBLICATIONS

European Journal of Biochemistry, vol. 230, No. 1, May 1995, pp. 38–44; Murby, M. et al.; 'Hydrophobicity engineering to increase solubility and stability of a recombinant protein from respiratory synctial virus'.

Journal of Biotechnology, vol. 42, No. 3, Oct. 16, 1995, pp. 207–219; Nguyen Ngoc, T. et al.; 'Hydrophobicity engineering to facilitate display of heterologous gene products on Staphylococcus xylosus'.

Journal of Cellular Biochemistry, vol. Supplement O, No. 19A, Jan. 5, 1995, p. 264; Stahl, S. et al.; 'Staphylococcus carnosus with surface–displayed recombinant immunogens, a novel live vector for subunit vaccine delivery'.

Journal of Bacteriology, vol. 177, No. 6, Mar. 1995, pp. 1470–1476; Samuelson, P. et al.; 'Cell surface display of recombinant proteins on Staphylococcus carnosus'.

Journal of Bacteriology, vol. 174, No. 13, Jul. 1992, pp. 4239–4245; Hansson, M. et al.; 'Expression of recombinant proteins on the surface of the coagulase–negative bacterium Staphylococcus xylosus'.

Virology, vo. 185, No. 2, Dec. 1991, pp. 749–757; Trudel, M. et al.; 'Protection of Balb–C mice from respiratory syncytial virus derived from the G glycoprotein'.

Gene., vol. 128, No. 1, 1993 Amsterdam NL, pp. 89–94; Nguyen, T. N. et al.; 'Cell–surface display of heterologous epitopes on Staphylococcus xylosus as a potential delivery system for oral vaccination'.

Journal of General Virology, vol. 74, No. 3, Mar. 1993 Reading GB, pp. 453–458; Martin–Gallardo, A. et al.; 'Expression of the G glycoprotein gene of human respiratory syncytial virus in Salmonella typhimurium'.

*Primary Examiner*—Ali Salimi
*Attorney, Agent, or Firm*—Rockey, Milnamow & Katz

[57] ABSTRACT

A method for obtaining a Staphylococcus carnosus bacterium expressing at its membrane surface a recombinant polypeptide derived from RSV protein G, said polypeptide having a sequence which is a modification of SEQ ID No. 1 and SEQ ID No. 2 (sequence encompassed between residues 130 and 230 of RSV A and RSV B protein G respectively) wherein at least one of position 44 and 57 is serine is disclosed.

6 Claims, 7 Drawing Sheets

METHOD FOR OBTAINING A PEPTIDE DERIVED FROM THE RESPIRATORY SYNCYTIAL VIRUS POLYPEPTIDE AND BACTERIUM EXPRESSING IT

CROSS-REFERENCE TO RELATED APPLICATIONS

This application is filed under Sec. 371 as a National Stage of International Application No. PCT/FR95/01465, filed Nov. 7, 1995.

FIELD OF THE INVENTION

The present invention relates to a method of recombinant DNA technology enabling point modifications of nucleotides to be introduced by directed mutagenesis into a gene coding for a polypeptide sequence, which is useful, in particular, for obtaining oral vaccines against the respiratory syncytial virus (RSV); it also relates to peptides and recombinant bacteria capable of being obtained by this method, to compositions containing them and also to the corresponding nucleotide sequences.

BACKGROUND OF THE INVENTION

Respiratory syncytial virus (RSV) is the commonest cause of respiratory ailments in newborn infants: bronchopneumopathies (bronchiolitis). The WHO estimates that 50 million individuals are affected by RSV every year, of whom 160,000 die worldwide. There are two subgroups of the virus (subgroups A and B).

RSV is classified in the family Paramyxoviridae, genus Pneumovirus, containing an unsegmented RNA genome of negative polarity coding for 10 specific proteins.

No vaccine against RSV is currently available. Vaccines containing inactivated virus have been shown to be ineffective and have even sometimes aggravated the infections of newborn infants. In the 1960s, the attempts at vaccination with formalin-inactivated RSV led to failure: instead of conferring protection on reinfection due to RSV, the vaccine had the effect of aggravating the ailment in the child.

Application WO 87/04185 proposed the use of RSV structural proteins for the purpose of a vaccine, such as the envelope proteins known as F protein (fusion protein) or G protein, a 22-kD glycoprotein, a 9.5-kD protein or the major capsid protein (N protein).

Application WO 89/02935 describes the protective properties of the whole F protein of RSV, where appropriate modified in monomeric or deacetylated form.

A series of fragments of the F protein has been cloned for the purpose of investigating their neutralizing properties.

However, the immune vaccines tested hitherto have been shown to be ineffective or have induced a pulmonary pathology (bronchiolitis or peribronchitis).

At the present time, no treatment of primary choice exists for infections due to RSV.

RSV infections of the upper airways: treatment is based essentially on symptomatic medication identical to that used for other viral infections.

RSV infections of the lower airways: treatment in newborn infants is based on the maintenance of correct hydration, the suctioning of secretions and the administration of oxygen if necessary. A positive effect has been observed with ribavirin, a nucleotide which is active in vitro against RSV.

In order to facilitate the administration of the vaccine, it would be desirable to have at one's disposal a product which is active via the oral route, generating a good immunity with reduced side effects.

BRIEF SUMMARY OF THE INVENTION

For this reason, the subject of the present invention is a method for obtaining a peptide or a protein, characterized in that:

a) a DNA sequence coding for a heterologous polypeptide carried by a peptide sequence flanked by amino acid residues 130 and 230 of the G protein of the respiratory syncytial virus, or a peptide sequence displaying at least 80% homology with the said peptide sequence, b) the means enabling the polypeptide to be expressed at the surface of the membrane of the bacterium, are introduced into a bacterium which is non-pathogenic for mammals.

It will thus be possible to observe an immune response against the said heterologous polypeptide during its administration, without using an adjuvant.

Advantageously, the heterologous peptide may be expressed fused with a fragment enabling its anchorage in the membrane of the bacterium.

The G protein is a methionine-poor envelope glycoprotein of RSV, of molecular weight between 84 and 90 kD. The sequence of the G protein differs for the subgroups A and B of RSV; the term "sequence of the G protein", when employed in the present application, should be understood to refer to the sequence of either subgroup A or subgroup B where not otherwise specified.

The Applicant has demonstrated that the sequence flanked by amino acids 130 and 230 of the natural G protein is especially suitable for inducing an effective protection against RSV infection, subgroups A and B, without inducing the pathologies observed with vaccines based on the formalin-inactivated whole virus, or observed with the whole F and G proteins.

The means enabling the polypeptide to be expressed are known to a person skilled in the art, and are adapted in accordance with the bacterium used.

Preferably, the DNA sequence is introduced in the form of a plasmid, such as a shuttle plasmid.

According to another aspect of the invention, the DNA sequence is integrated into the chromosome of the bacterium.

DETAILED DESCRIPTION OF THE INVENTION

RSV proteins have, to date, been expressed in various expression systems, such as vaccinia virus, baculoviruses or adenoviruses. However, some potential problems are associated with the presence of residual viral particles.

The method according to the present invention employs bacteria which are commensal with man, nonpathogenic and edible. Preferably, Gram-positive bacteria are used, in particular the bacteria may belong to the genus Staphylococcus. *Staphylococcus xylosus* and *Staphylococcus carnosus* which are bacteria which have been used in the food industry for many years and may be administered live via the oral route. Systems for the expression of heterologous epitopes at the surface of *S. xylosus* have been described, in particular, by N'guyen et al. in Gene, 1993, 128, 89–94, and for *S. carnosus* by Samuelsson et al. in *J. Bacteriol.*, 1995, 177, 1470–1476.

Preferably, the heterologous polypeptide is expressed at the surface of the membrane of the bacterium, in a conformation which is essentially identical to that of the corresponding epitope of the natural G protein.

The presentation of the recombinant protein at the membrane surface of the bacterium depends on its chemical nature and on its peptide arrangement.

It is possible to use the natural sequence of the RSV G protein, and to introduce a DNA sequence coding for a peptide containing the sequence ID No. 1 or the sequence ID No. 2.

According to an aspect of the invention, in the sequence corresponding to the sequence flanked by amino acids 130 and 230 of the G protein, the amino acid cysteine at positions 173 and/or 186 has been replaced by an amino acid which does not form a disulphide bridge, especially serine.

Figure 1:
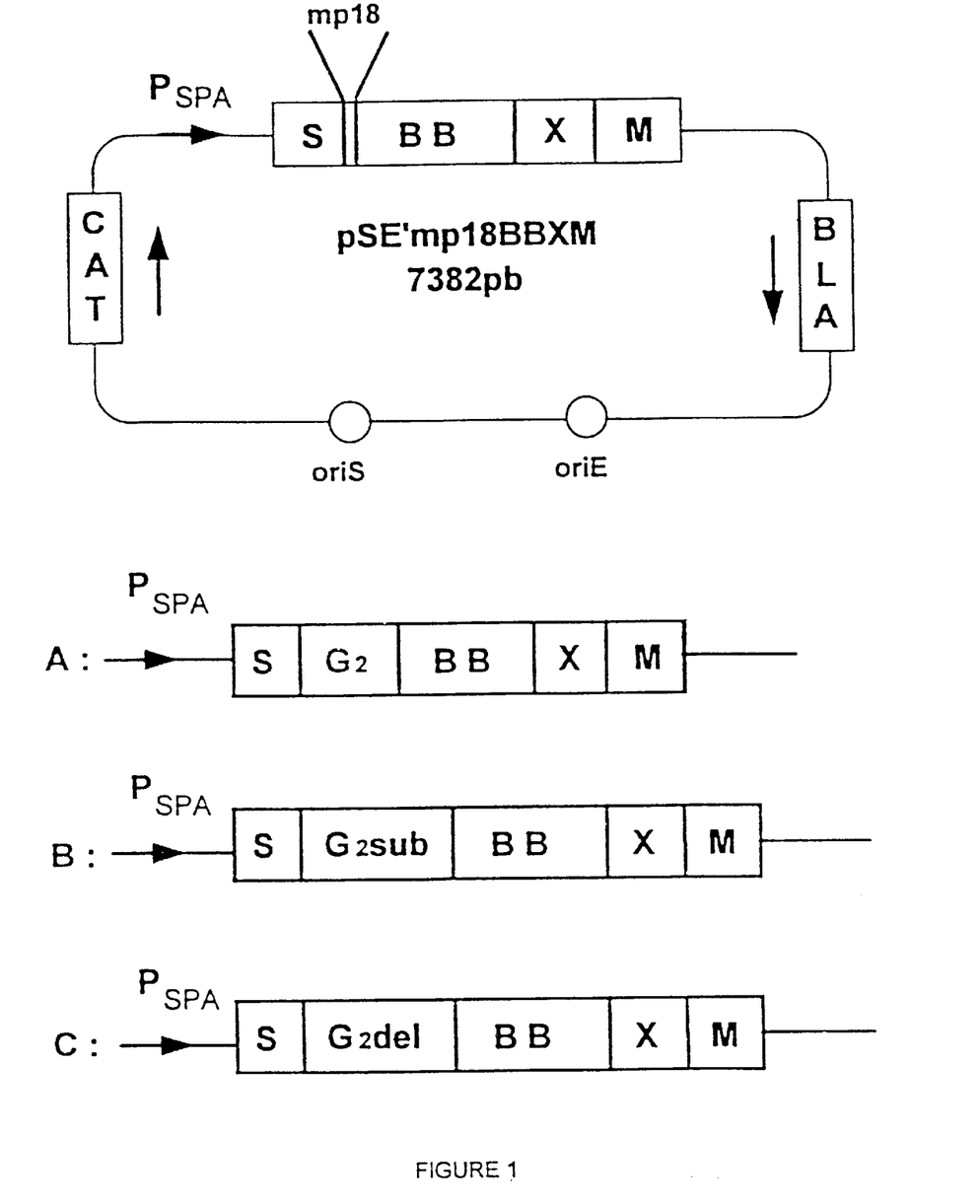
FIG. 1: Construction of the shuttle vector pSE'mp18BBXM.
Figure 2:
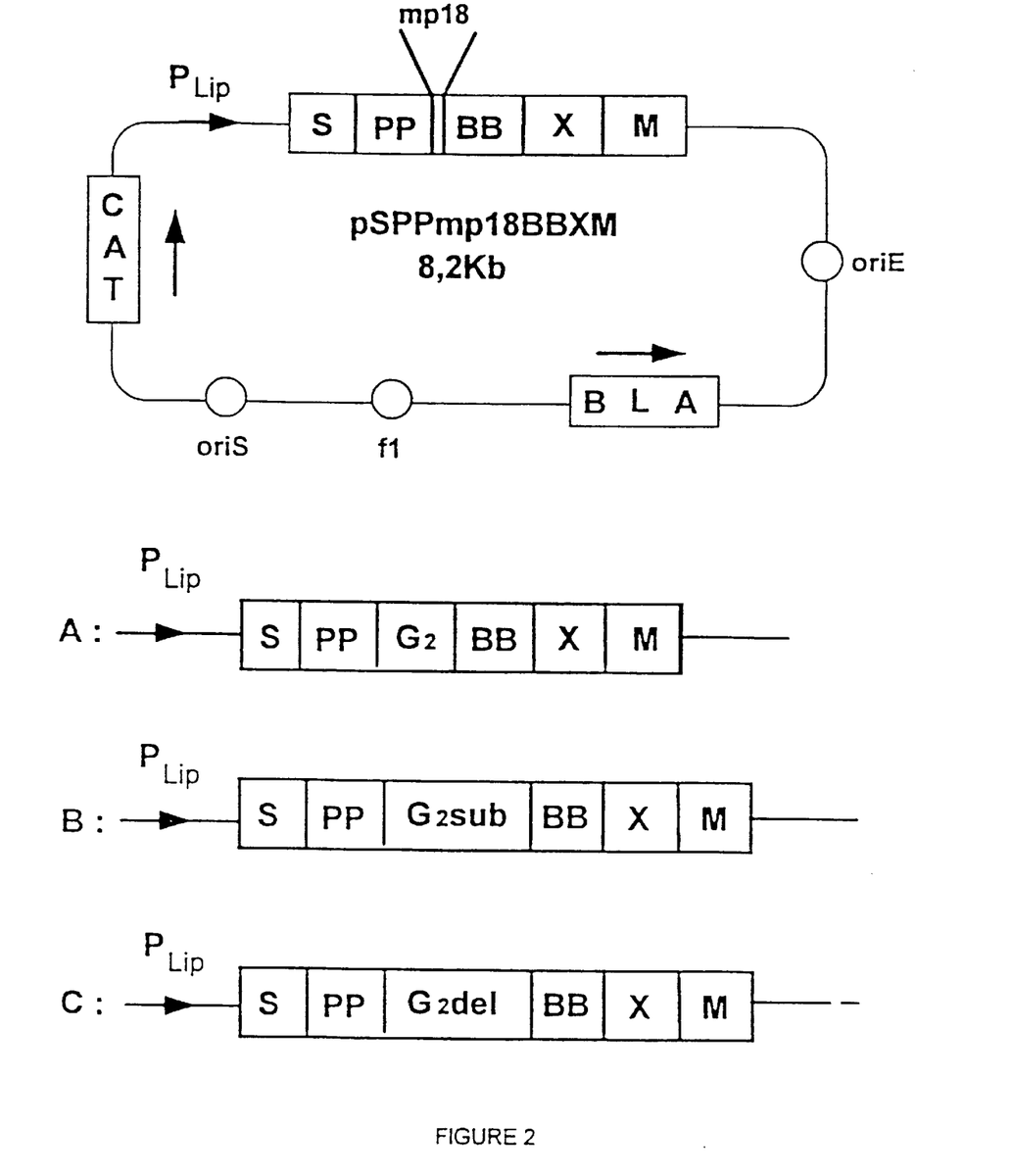
FIG. 2: Construction of the shuttle vector pSPPmp18BBXM.

Such a mutation favours the formation of the disulphide bridge between the cysteine residues remaining at positions 176 and 182, which is critical for the immunogenicity of the sequence; it avoids the formation of haphazard disulphide bridges (A: FIGS. 1 and 2).

Peptides which are useful for carrying out such a method are those containing, in particular, one of the sequences ID No. 3 or ID No. 4.

According to another aspect of the invention, in the sequence of the heterologous polypeptide corresponding to the RSV G protein, the amino acids phenylalanine corresponding to positions 163, 165, 168 and/or 170 of the sequence of the G protein are replaced by a polar amino acid, especially serine (B: FIGS. 1 and 2).

This modification may be combined with the mutations mentioned above. Such a polypeptide can, in particular, possess the sequence ID No. 5.

When the method is carried out, the elimination of the hydrophobic region located in proximity to the critical loop between the two amino acids cysteine at positions 176 and 182 enables the recombinant protein to cross the bacterial membrane more easily and to expose the immunodominant portion correctly at the membrane surface.

According to yet another aspect of the invention, in the peptide sequence corresponding to the RSV G protein, the sequence flanked by the amino acids numbered 162 and 170 is deleted (C: FIGS. 1 and 2).

More especially, the sequence of the heterologous peptide expressed in the bacterium can contain the sequence ID No. 6.

In all cases, sequences displaying at least 80% and preferably at least 90% homology with the abovementioned sequences are adapted to the carrying out of the invention. They comprise especially the sequences resulting from point mutations in the nucleotide sequence and including the replacement of at least one amino acid by an equivalent amino acid; equivalent amino acid is understood to mean a molecule having an analogous chemical structure and a similar molecular weight.

The invention also comprises a bacterium expressing a peptide or a protein, capable of being obtained by the method described in the present application. The said bacterium can be live or killed.

According to an advantageous aspect of the invention, the DNA sequence introduced into the bacterium leads to the expression of the heterologous polypeptide in the form of a fusion protein. There is then incorporated into the construct a sequence coding for another peptide, which will act as "spacer" or spacer component and will enable optimum presentation of the heterologous polypeptide at the surface of the bacterium. A protein which may be advantageously used as "spacer" is a human serum albumin binding protein, in particular the G protein of streptococcus (designated in the text which follows by BB), or one of its fragments. The fusion of the heterologous polypeptide with the spacer element takes place at the C-terminal end of the said polypeptide, in order to enhance the accessibility of the antigen to the immune system.

The polypeptides or bacteria displaying one or more of the above features are useful as a medicinal product.

The invention comprises pharmaceutical compositions, characterized in that they comprise a polypeptide or a bacterium according to the invention, mixed with pharmaceutically acceptable adjuvants.

The oral vaccine based on live vector must comprise the modified protein which possesses the optimal conformation for inducing the best protection against RSV.

Thus, the subject of the present invention is also an application of such a pharmaceutical composition to the preparation of an oral vaccine intended for preventing infections caused by the respiratory syncytial virus. According to another aspect, the subject of the invention is the application of such a composition to the preparation of a vaccine for parenteral, enteral or mucosal administration intended for preventing infections caused by the respiratory syncytial virus.

Lastly, the subject of the invention is the nucleotide sequences coding for a polypeptide carried by a peptide sequence flanked by amino acid residues 130 and 230 of the G protein of the respiratory virus, or for a polypeptide displaying at least 80% homology with the said peptide sequence, and containing, in addition, the means enabling the polypeptide to be expressed at the surface of the membrane of a non-pathogenic bacterium of the genus Staphylococcus.

The examples which follow are intended to illustrate the invention without in any way limiting its scope.

BRIEF DESCRIPTION OF THE DRAWINGS

In these examples, reference will be made to the following figures.

EXAMPLE 1

A—Gene construction: Materials and Methods

In an Eppendorf microtube, 300 μg of beads are rinsed with washing/binding buffer (1 M NaCl, 10 mM Tris-HCl pH 7.5, 1 mM EDTA) before adding 0.2 pmol of the biotinylated oligonucleotide, and the mixture is incubated for 15 minutes at room temperature for binding. The beads with the bound oligonucleotide are rinsed and sedimented. 0.2 pmol of the next oligonucleotide phosphorylated at the 5' end is added in 60 μl of hybridization/ligation buffer (50 mM Tris-HCl pH 7.6, 10 mM $MgCl_2$, 1 mM ATP, 1 mM 1,4-dithiothreitol [DTT], 5% polyethylene glycol [PEG] 8000). The hybridization mixture is incubated at 70° C. for 5 min, and allowed to return to 37° C. before adding 3 units of T4 DNA ligase (BRL), followed by 15 min of incubation at 37° C. The reaction mixture is rinsed before adding 0.2 pmol of the next oligonucleotide. The hybridization/ligation procedure is repeated each time a new complementary oligonucleotide phosphorylated at the 5' end is added. At the end, the DNA duplex bound to magnetic beads may be separated from the support by cutting with suitable restriction enzymes.

B—Construction of the *S. Xylosus* Shuttle Vector

An oligonucleotide linker (5'-AGCTTGGCTG TTCCGCCATGGCTCGAG-3'(SEQ ID NO: 7), with the complementary strand) is inserted into the HindIII site of plasmid pSZZmp18XM (Hansson et al., 1992, *J. Bacteriol*, 174: 4239–4245), thereby creating two additional restriction sites, NcoI and XhoI, downstream of the HindIII site of the resulting vector pSZZmp18(XhoI)XM. A gene fragment coding for 198 amino acids, designated BB, of the serum albumin-binding region of the streptococcal G protein (Nygren et al., 1988 *J. Mol. Reconig.*, 1:69–74) is generated by PCR with the primers (1=5'-CCGAATTCAA GCTTA-GATGC TCTAGCAAAA GCCAAG-3'(SEQ ID NO: 8 and 2=5'-CCCCTGCAGT TAGGATCCCT CGAGAGGTAA TGCAGCTAAA ATTTCATC-3'(SEQ ID NO: 9) on the plasmid template pSPG1 (Guss et al., 1986, *EMBO J.* 5 : 1567–1575). The fragment is digested with HindIII and XhoI and cloned downstream of the multiple cloning site mp18 of the vector pSZZmp18-(XhoI)XM; the resulting vector pSZZmp18(XhoI)BBXM is digested with NotI and HindIII. The fragment containing ZZ is replaced by another fragment, digested with the same restriction enzymes, of the vector pE'mp18 (Sophia Hober, unpublished). The resulting vector is designated pSE'mp18BBXM (FIG. 1).

C. Construction of the *S. Carnosus* Shuttle Vector

The plasmid pLipPS17 (Demleitner et al 1994, *FEMS Microbiol. Lett.* 121: 189–198) is constructed from the vector pLipPS1 (Liebl et al. 1986. *Mol. Gen. Genet* 204: 166–173) by introducing a BsmI restriction site at the beginning of the signal sequence of the lipase, a BclI site at the end of the signal sequence, and a BglII site at the end of the region coding for the propeptide by directed mutagenesis in vitro. A gene fragment constituting the entire *S. carnosus* vector pLipPS17, except a fragment coding for the C-terminal portion of the propeptide and the majority of the mature lipase of *S. hyicus*, is isolated by a SalI-HindIII digestion and ligated into the plasmid pRIT28 previously digested with the same enzymes. The resulting plasmid, designated pSLip, contains the origin of replication of both *E. coli* and *S. aureus*. In order to restore the C-terminal region of the propeptide of the lipase, a gene fragment coding for the C-terminal portion is generated by PCR with the primers (1:5' CCGAATTCTCGAGGCTCCTAAAGAAAATAC-3'(SEQ ID NO: 10) and 2: 5' -CCAAGCTTGGATCCTGCGCAGATCTTGGTGTTGG TTTTTTG-3'(SEQ ID NO: 11)) on the pLipPS17 plasmid template, thus creating two EcoRI and XhoI restriction sites downstream and FspI, BamHI and HindIII restriction sites upstream. The gene fragment coding for the C-terminal portion of the propetide is digested with EcoRI/HindIII and cloned into the vector pRIT28 in order to check the sequence and then XhoI/BamHI digested and transferred into the SalI/BamHI restriction sites of the vector pSLip. The resulting plasmid pSPP is digested with HindIII, complemented by the Klenow polymerase enzyme and religated in order to give the plasmid pSPPHindIII. The shuttle vector pSPPmp18BBXM (FIG. 2) is constructed by NotI digestion of pSPPHindIII, followed by filling, digested with BamHI and ligated with a BamHI/EcoRV fragment isolated from pSE'mp18BBXM.

EXAMPLE 2

Extraction and Analysis of Membrane Proteins of Recombinant *S. xylosus* bacteria:

In a 1-liter Erlenmeyer, 250 ml of medium (7.5 g of TSB, 12.5 g of yeast extract) containing chloramphenicol (20 µg/ml) are inoculated with 5 ml of preculture (overnight) of *S. xylosus* transformed with the shuttle vector pSE'G2BBXM or pSE'G2subBBXM or pSE'G2delBBXM according to the protocol of Götz et al., 1981, *J. Bacteriol*, 145:74–81. The medium is incubated with stirring at a temperature of 32° C. for a period of 6 hours. It is centrifuged at 5000 rpm for 12 minutes and at a temperature of 4° C. The bacterial pellet is resuspended in 40 ml of TST, and 200 µl of solution containing lysostaphin (1 mg/ml) and 200 µl of lysozyme (50 mg/ml) are added. The medium is incubated for one hour at a temperature of 37° C. with moderate agitation. The solution is sonicated for 2 min with a Vibra cell apparatus equipped with a probe whose power is adjusted to 7. The suspension is centrifuged at 13,500 rpm for 20 min at a temperature of 4° C. The proteins are purified by affinity: the supernatant is passed through an HSA (human serum albumin)—Sepharose affinity column. After the column is rinsed, the proteins are eluted with an acid buffer at pH 2.7 and lyophilized.

The proteins are separated on two identical SDS-PAGE (12%) gels with the precoloured standard molecular size markers (Gibco BRL). One gel is stained with Coomassie blue. The other one is transferred onto a Problot™ membrane (Applied Biosystem) for immunoblotting with anti-G1 specific antibody (obtained from the serum of a rabbit immunized with the G1 peptide (aa174–187) according to conventional immunization protocols). See FIG. 3.

EXAMPLE 3

Analysis by flow cytometry (FACScan™) of recombinant proteins at the surface of *S. xylosus*

Figure 4:
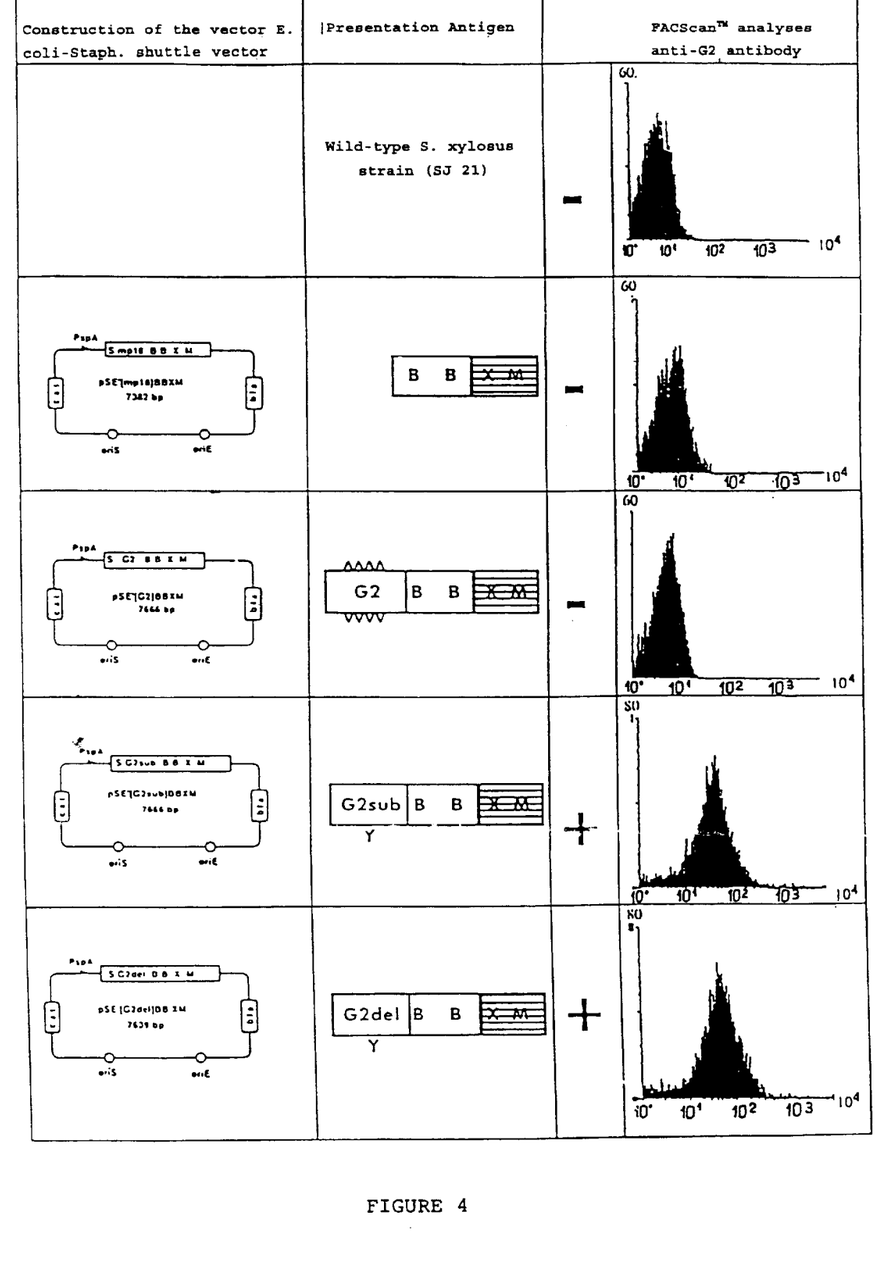
FIG. 4: Analysis by flow cytometry of the recombinant proteins at the surface of S. xylosus.

Culturing of recombinant *S. xylosus* bacteria is carried out as described above. To make a stock solution, the bacterium is resuspended in PBS solution containing 0.1% of sodium azide (w/v) at a final concentration estimated by an optical density (600 nm) equal to unity. 30 µl of stock solution are aliquoted into each conical well of a microtitration plate, and centrifugation is performed at 550 g for 10 minutes at 4° C. The bacterial pellet is resuspended in a volume of 150 µl of PBS solution containing rabbit anti-G2 polyclonal serum (titre ¹⁄₁,₂₈₀,₀₀₀) diluted to ¹⁄₂₀₀, incubating for 30 minutes. The bacterial cells are rinsed twice with PBS and incubated in 150 µl of PBS solution containing FITC-anti-rabbit (Sigma) diluted to ¹⁄₁₀₀ for a period of 30 minutes. After the cells have been rinsed twice with the PBS buffer, they are resuspended in a Falcon tube containing 1 ml of PBS-1% (w/v) paraformaldehyde buffer. The samples prepared are analysed on a FACScan™ apparatus (Becton Dickinson). The fluorescence distribution of each cell suspension is analysed with LYSIS II™ software, and is represented by fluorescence histograms. See FIG. 4.

EXAMPLE 4

Analysis by flow cytometry (FACscan™) of the recombinant proteins at the surface of *S. carnosus*

Figure 5:
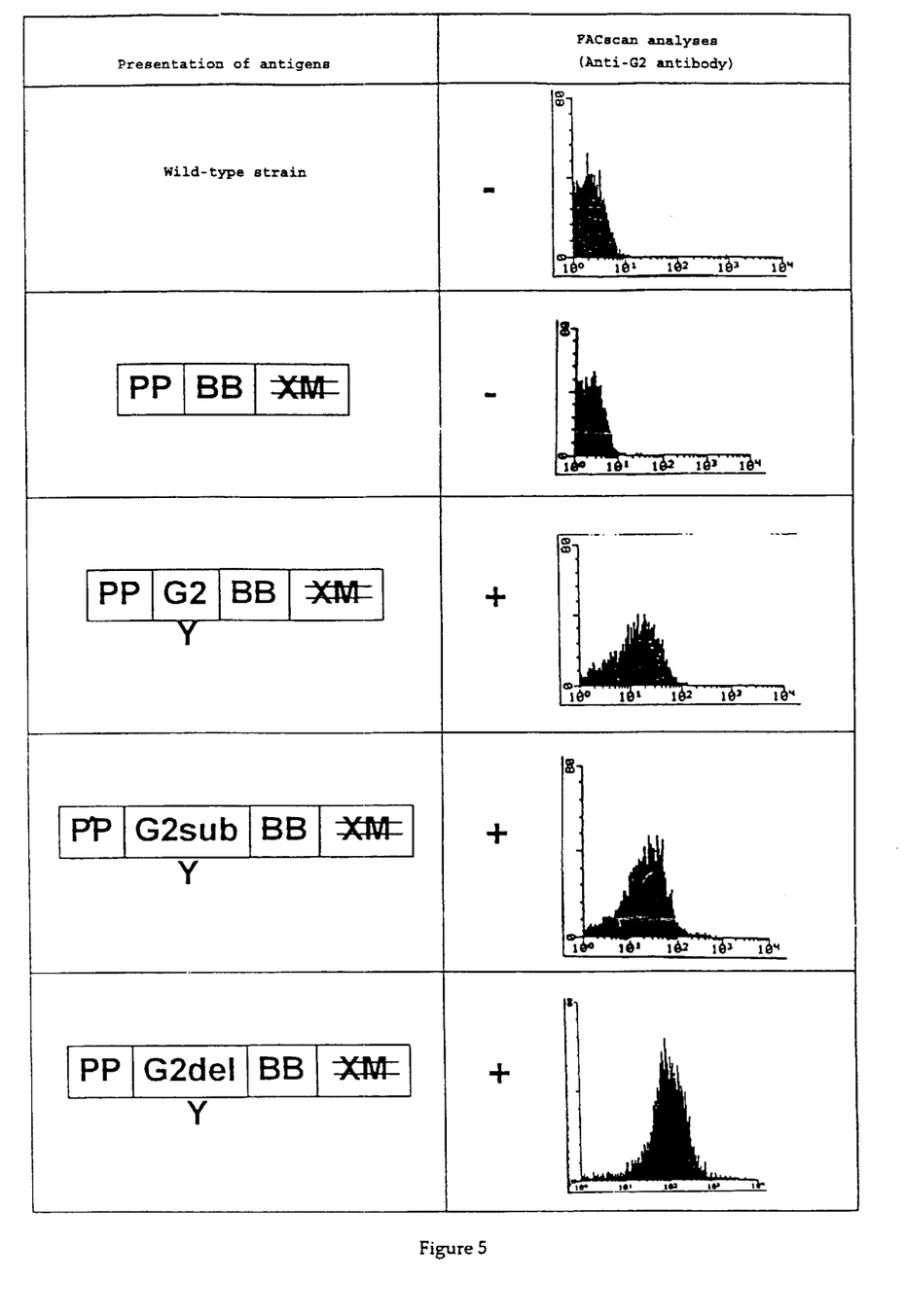
FIG. 5: Analysis by flow cytometry of the recombinant proteins at the surface of S. carnosus.

Culturing of the recombinant *S. carnosus* bacteria transformed with the shuttle vector pSPPG2BBXM, or pSPPG2subBBXM, or pSPPG2delBBXM are carried out as described in Example 2. The FACscan analysis is identical to that used in Example 3, the only difference being that the bacterial pellet is resuspended in a volume of 150 μl of PBS solution containing mouse anti-G2 monoclonal serum (860 μg/μl) diluted ¹⁄₄₀₀, incubating for 60 minutes. The fluorescence distribution of each cell suspension is analysed with LYSIS II™ software and is represented by fluorescence histograms. See FIG. 5.

EXAMPLE 5

Immune response of mice immunized by the oral route with *S. carnosus* expressing the BB antigen at their surface.

Batches of 5 BALB/c or C572B1/6 mice received 8 oral administrations (gastric intubation), at the rate of one per week, of $10^{10}$ *S. carnosus*, transformed with the vector pSPPBBXM, per mouse in 0.5 ml.

The assay of the anti-BB IgG serum antibodies is determined by the ELISA test.

100 μl of BB at 1 μg/ml per well are adsorbed by incubating overnight at 4° C. The microplate is then rinsed three times with 1 X PBS. 200 μl of PBS-gelatin at 0.5% are added to each well; after incubating for 90 minutes at 37° C., the wells are rinsed three times with 1 X PBS. The sera to be tested are then deposited into the wells, then incubated for 2 hours at room temperature and rinsed three times with 1 X PBS. The revealing is obtained by depositing 100 μl of peroxidase-conjugated mouse anti-Ig antibody, incubated for 60 minutes at room temperature and then rinsing three times with 1 X PBS. The secondary antibody is revealed by depositing into all the wells 100 μl of TMB Microwell substrate and then the enzymatic reaction is plugged by adding 100 μl of 1 M $H_2SO_4$, into all the wells of the microplate. The reading of the results is carried out at 450 nm with the DYNATECH MR5000 or LABSYSTEMS iEMS plate reader).

The assay of the anti-staphylococcus IgG serum antibodies is determined by ELISA as described above. The antigens adsorbed are whole Staphylococci at the concentration of $10^8$ bacteria per well. The results are read at 450 nm with the DYNATECH MR5000 or LABSYSTEMS iEMS plate reader).

Figure 6A:
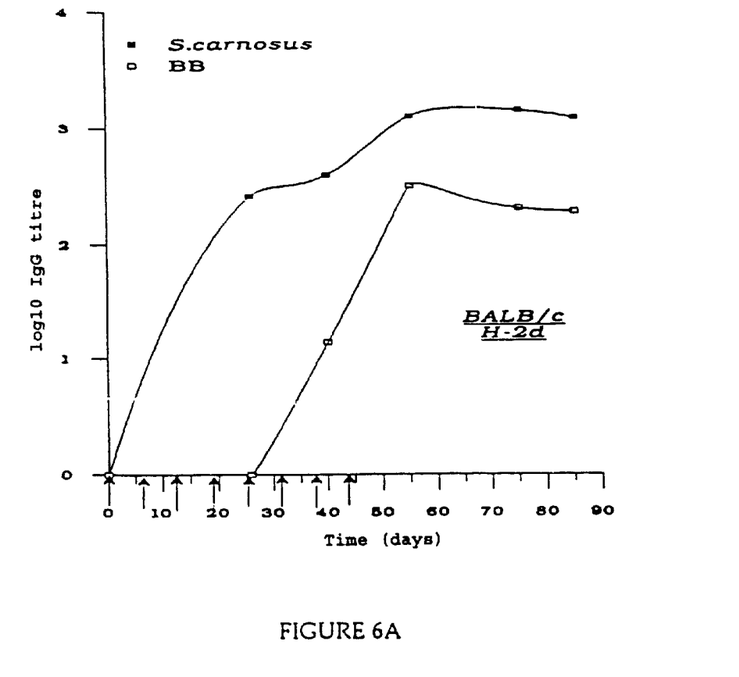
FIG. 6a: Antibody response induced by S. carnosus and the BBprotein in BALB/c mice.
Figure 6B:
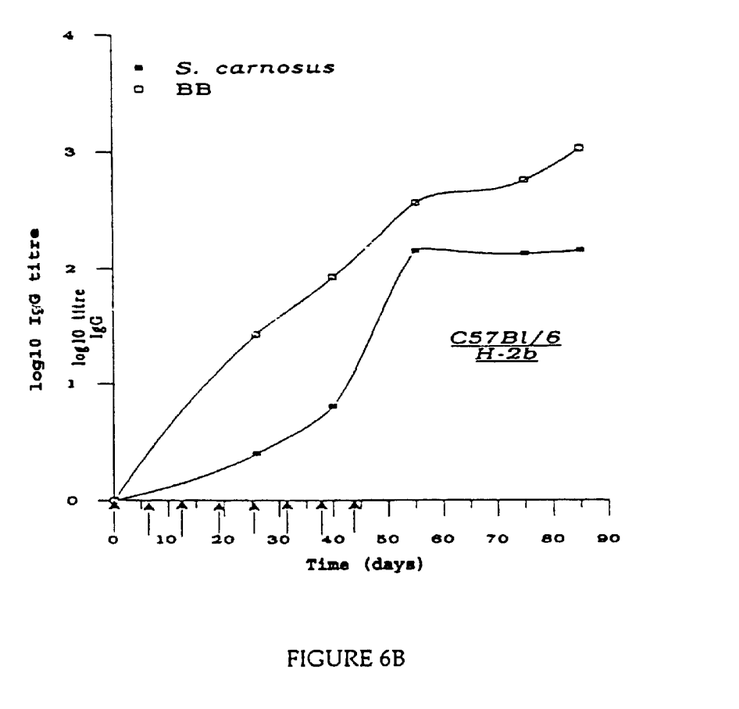
FIG. 6b: Antibody response induced by S. carnosus and the BB protein in C572B/6 mice.
Figure 7:
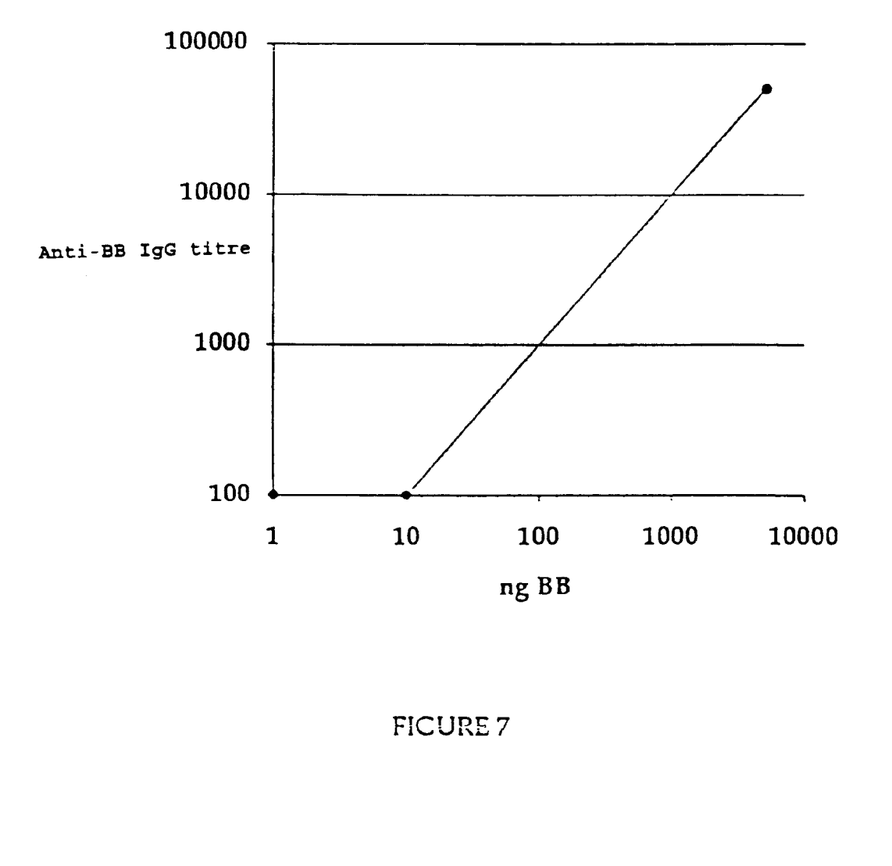
FIG. 7: Antibody response induced by the BB protein.

The antibody responses induced in mice are represented in FIGS. 6a and 6b.

EXAMPLE 6

Adjuvant effect of the live vector

BALB/c mice (N=5) receive 3 subcutaneous injections of BB in the presence of Preund's adjuvants. Blood is collected individually at D38 and the anti-BB titres are determined by ELISA as described in Example 5. Example 7 shows that 3 subcutaneous injections of 10 ng of BB do not induce antibody response. On the other hand, three injections of $10^9$ *S. xylosus* expressing BB at its surface induce an anti-BB titre of ¹⁄₁₀₀₀₀.

*S. xylosus* potentiates the immunogenicity of the antigen which it expresses.

Figure 3:
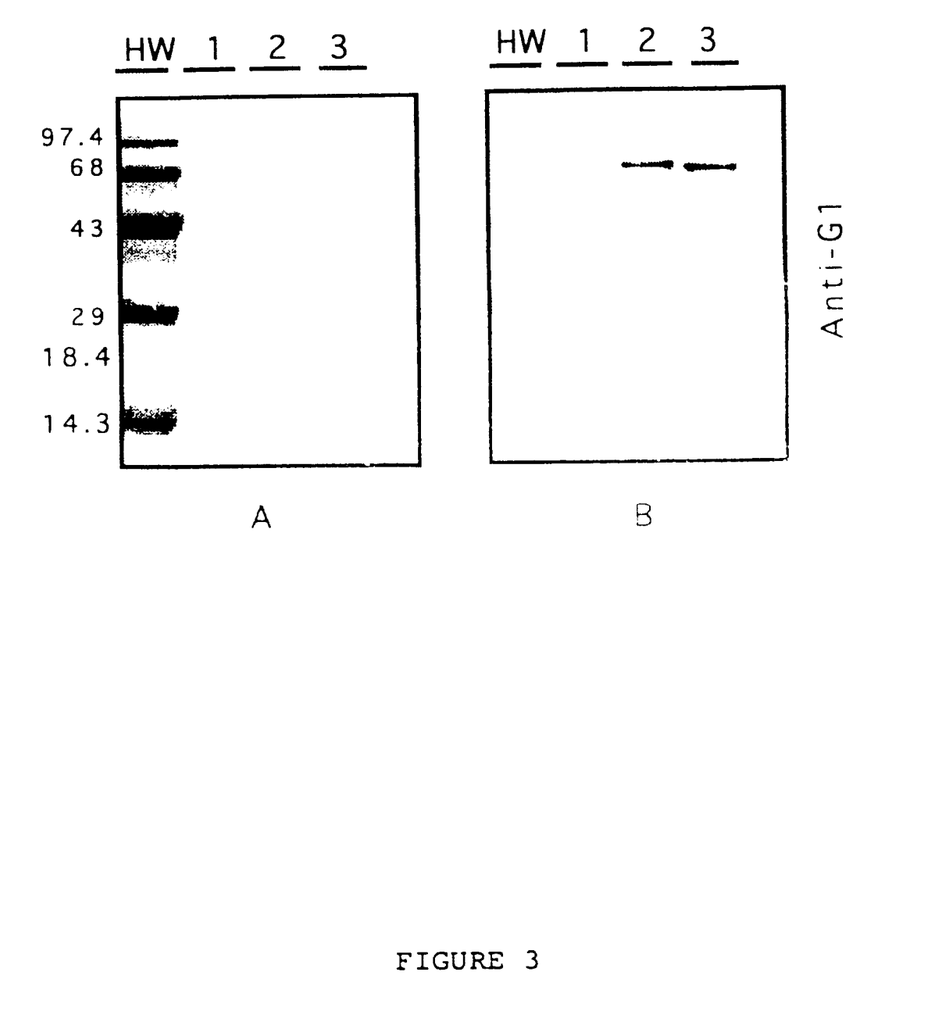
FIG. 3: Extraction and analysis of the surface recombinant membrane proteins of S. xylosus.

LEGEND TO FIG. 3

A) Coomassie blue staining: SDS-Page gel of the fusion proteins extracted from bacterial membrane and affinity purified on Albumin column of the different constructs:

Well HW: molecular size markers (in Kda),

Well 1: *S. xylosus* [pSE'G2BBXM],

Well 2: *S. xylosus* [pSE'G2subBBXM],

Well 3: *S. xylosus* [pSE'G2delBBXM].

B) Immunoblot of the fusion proteins extracted from bacterial membrane and affinity purified on Albumin column of the different constructs with rabbit anti-G1 polyclonal antibody.

Well HW: molecular size markers (in Kda),

Well 1:*S. xylosus* [pSE'G2BBXM],

Well 2:*S. xylosus* [pSE'G2subBBXM],

Well 3:*S. xylosus* [pSE'G2delBBXM].

What is claimed is:

1. A method for obtaining a *Staphylococcus carnosus* bacterium expressing at its membrane surface a recombinant polypeptide derived from the respiratory syncytial virus protein G, comprising introducing into said bacterium:

a DNA sequence coding for a polypeptide having an amino acid sequence which is a modification of SEQ ID NO: 1 or SEQ ID NO: 2, wherein at least one of position 44 and position 57 is serine.

2. A method according to claim 1, characterized in that the DNA sequence coding for the polypeptide is linked to a sequence coding for a spacer polypeptide fragment and said sequences will be expressed in the form of a fusion protein, the spacer fragment being linked to the C-terminal end of the heterologous polypeptide.

3. A method according to claim 1, characterized in that the recombinant polypeptide expressed at the surface of the membrane of the *Staphylococcus carnosus* bacterium is capable of recognizing antibodies raised against a polypeptide having the amino acid sequence SEQ ID NO: 3 or SEQ ID NO: 4.

4. A method according to claim 1, characterized in that the DNA sequence is introduced into the bacterium in the form of a plasmid.

5. A method according to claim 1, characterized in that the DNA sequence is introduced by integration into the chromosome of the bacterium.

6. A method for obtaining a *Staphylococcus carnosus* bacterium expressing at its membrane surface a recombinant polypeptide derived from the respiratory syncytial virus protein G, comprising introducing into said bacterium:

a DNA sequence coding for a polypeptide having an amino acid sequence SEQ ID NO: 3 or SEQ ID NO: 4.

* * * * *

UNITED STATES PATENT AND TRADEMARK OFFICE
CERTIFICATE OF CORRECTION

PATENT NO. : 6,130,091

DATED : October 10, 2000

INVENTOR(S) : Binz, et al.

It is certified that error appears in the above-identified patent and that said Letters Patent is hereby corrected as shown below:

Cover Page, please insert --U.S. Patent No. 5,149,659 (Wertz et al.)--
Column 4, line 51, please delete "S. *carnosus*and" and insert --S. *carnosus* and--
Column 4, line 59, please delete "Materials and Methods" and insert --Material and methods--
Column 5, line 25, please delete "GATGCTCTAGCAAAAGCCAAG-3'(SEQ ID NO:8 and" insert --GATGCTCTAGCAAAAGCCAAG-3'(SEQ ID NO:8) and--
Column 5, line 27, please delete "TGCAGCTAAA ATTTCATC-3'" and insert --TGCAGCTAAA ATTTCATC-3)--
Column 5, line 48, please delete "SaII-HindIII" and insert --SalI-HindIII--
Column 6, line 2, please delete "pSPPIIindIII" and insert --pSPPHindIII--
Column 6, line 23, please delete "2 min" and insert --2 min.--
Column 6, line 26, please delete "2 min" and insert --2 min.--
Column 7, line 15, please delete "(gastric intubation)," and insert --(gastric incubation),--
Column 8, line 11, please delete "Preund's" and insert --Freund's--

Signed and Sealed this

Seventeenth Day of April, 2001

Attest:

NICHOLAS P. GODICI

Attesting Officer

Acting Director of the United States Patent and Trademark Office

SEQUENCE LISTING (1) GENERAL INFORMATION:

(iii) NUMBER OF SEQUENCES: 11

(2) INFORMATION FOR SEQ ID NO:1:

(i) SEQUENCE CHARACTERISTICS:
      (A) LENGTH: 303 base pairs
      (B) TYPE: nucleic acid
      (C) STRANDEDNESS: single
      (D) TOPOLOGY: linear    (ii) MOLECULE TYPE: cDNA    (ix) FEATURE:
      (A) NAME/KEY: CDS
      (B) LOCATION: 1..303

(xi) SEQUENCE DESCRIPTION: SEQ ID NO:1:

```
ACC GTG AAA ACC AAA AAC ACC ACG ACC ACC CAG ACC CAG CCG AGC AAA      48
Thr Val Lys Thr Lys Asn Thr Thr Thr Thr Gln Thr Gln Pro Ser Lys
 1               5                  10                  15

CCG ACC ACC AAA CAG CGT CAG AAC AAA CCG CCG AAC AAA CCG AAC AAC      96
Pro Thr Thr Lys Gln Arg Gln Asn Lys Pro Pro Asn Lys Pro Asn Asn
             20                  25                  30
```

```
GAT TTC CAT TTC GAA GTG TTC AAC TTC GTG CCG TGC AGC ATC TGC AGC        144
Asp Phe His Phe Glu Val Phe Asn Phe Val Pro Cys Ser Ile Cys Ser
        35                  40                  45

AAC AAC CCG ACC TGC TGG GCG ATC TGC AAA CGT ATC CCG AAC AAA AAA        192
Asn Asn Pro Thr Cys Trp Ala Ile Cys Lys Arg Ile Pro Asn Lys Lys
    50                  55                  60

CCG GGC AAA AAA ACC ACG ACC AAA CCG ACC AAA AAA CCG ACC TTC AAA        240
Pro Gly Lys Lys Thr Thr Thr Lys Pro Thr Lys Lys Pro Thr Phe Lys
65                  70                  75                  80

ACC ACC AAA AAA GAT CAT AAA CCG CAG ACC ACC AAA CCG AAA GAA GTG        288
Thr Thr Lys Lys Asp His Lys Pro Gln Thr Thr Lys Pro Lys Glu Val
                85                  90                  95

CCG ACC ACC AAA CCA                                                    303
Pro Thr Thr Lys Pro
            100

(2) INFORMATION FOR SEQ ID NO:2:

(i) SEQUENCE CHARACTERISTICS:
        (A) LENGTH: 303 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..303

(xi) SEQUENCE DESCRIPTION: SEQ ID NO:2:

ACC GCG CAG ACC AAA GGC CGT ATC ACC ACC AGC ACC CAG ACC AAC AAA         48
Thr Ala Gln Thr Lys Gly Arg Ile Thr Thr Ser Thr Gln Thr Asn Lys
1               5                  10                  15

CCG AGC ACC AAA AGC CGT AGC AAA AAC CCG CCG AAA AAA CCG AAA GAT         96
Pro Ser Thr Lys Ser Arg Ser Lys Asn Pro Pro Lys Lys Pro Lys Asp
            20                  25                  30

GAT TAC CAC TTC GAA GTG TTC AAC TTC GTG CCC TGC AGC ATC TGC GGC        144
Asp Tyr His Phe Glu Val Phe Asn Phe Val Pro Cys Ser Ile Cys Gly
        35                  40                  45

AAC AAC CAG CTG TGC AAA AGC ATC TGC AAA ACC ATC CCG AGC AAC AAA        192
Asn Asn Gln Leu Cys Lys Ser Ile Cys Lys Thr Ile Pro Ser Asn Lys
    50                  55                  60

CCG AAA AAG AAA CCG ACC ATC AAA CCG ACC AAC AAA CCG ACC ACC AAA        240
Pro Lys Lys Lys Pro Thr Ile Lys Pro Thr Asn Lys Pro Thr Thr Lys
65                  70                  75                  80

ACC ACC AAC AAA CGT GAT CCG AAA ACC CCG GCG AAA ATG CCG AAG AAG        288
Thr Thr Asn Lys Arg Asp Pro Lys Thr Pro Ala Lys Met Pro Lys Lys
                85                  90                  95

GAA ATC ATC ACC AAC                                                    303
Glu Ile Ile Thr Asn
            100

(2) INFORMATION FOR SEQ ID NO:3:

(i) SEQUENCE CHARACTERISTICS:
        (A) LENGTH: 303 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
```

(B) LOCATION: 1..303

(xi) SEQUENCE DESCRIPTION: SEQ ID NO:3:

ACC GTG AAA ACC AAA AAC ACC ACG ACC ACC CAG ACC CAG CCG AGC AAA         48
Thr Val Lys Thr Lys Asn Thr Thr Thr Thr Gln Thr Gln Pro Ser Lys
 1               5                  10                  15

CCG ACC ACC AAA CAG CGT CAG AAC AAA CCG CCG AAC AAA CCG AAC AAC         96
Pro Thr Thr Lys Gln Arg Gln Asn Lys Pro Pro Asn Lys Pro Asn Asn
                20                  25                  30

GAT TTC CAT TTC GAA GTG TTC AAC TTC GTG CCG AGC AGC ATC TGC AGC         144
Asp Phe His Phe Glu Val Phe Asn Phe Val Pro Ser Ser Ile Cys Ser
            35                  40                  45

AAC AAC CCG ACC TGC TGG GCG ATC AGC AAA CGT ATC CCG AAC AAA AAA         192
Asn Asn Pro Thr Cys Trp Ala Ile Ser Lys Arg Ile Pro Asn Lys Lys
        50                  55                  60

CCG GGC AAA AAA ACC ACG ACC AAA CCG ACC AAA AAA CCG ACC TTC AAA         240
Pro Gly Lys Lys Thr Thr Thr Lys Pro Thr Lys Lys Pro Thr Phe Lys
 65                  70                  75                  80

ACC ACC AAA AAA GAT CAT AAA CCG CAG ACC ACC AAA CCG AAA GAA GTG         288
Thr Thr Lys Lys Asp His Lys Pro Gln Thr Thr Lys Pro Lys Glu Val
                 85                  90                  95

CCG ACC ACC AAA CCA                                                     303
Pro Thr Thr Lys Pro
            100

(2) INFORMATION FOR SEQ ID NO:4:

(i) SEQUENCE CHARACTERISTICS:
            (A) LENGTH: 303 base pairs
            (B) TYPE: nucleic acid
            (C) STRANDEDNESS: single
            (D) TOPOLOGY: linear (ii) MOLECULE TYPE: cDNA (ix) FEATURE:
            (A) NAME/KEY: CDS
            (B) LOCATION: 1..303

(xi) SEQUENCE DESCRIPTION: SEQ ID NO:4:

ACC GCG CAG ACC AAA GGC CGT ATC ACC ACC AGC ACC CAG ACC AAC AAA         48
Thr Ala Gln Thr Lys Gly Arg Ile Thr Thr Ser Thr Gln Thr Asn Lys
 1               5                  10                  15

CCG AGC ACC AAA AGC CGT AGC AAA AAC CCG CCG AAA AAA CCG AAA GAT         96
Pro Ser Thr Lys Ser Arg Ser Lys Asn Pro Pro Lys Lys Pro Lys Asp
                20                  25                  30

GAT TAC CAC TTC GAA GTG TTC AAC TTC GTG CCC AGC AGC ATC TGC GGC         144
Asp Tyr His Phe Glu Val Phe Asn Phe Val Pro Ser Ser Ile Cys Gly
            35                  40                  45

AAC AAC CAG CTG TGC AAA AGC ATC AGC AAA ACC ATC CCG AGC AAC AAA         192
Asn Asn Gln Leu Cys Lys Ser Ile Ser Lys Thr Ile Pro Ser Asn Lys
        50                  55                  60

CCG AAA AAG AAA CCG ACC ATC AAA CCG ACC AAC AAA CCG ACC ACC AAA         240
Pro Lys Lys Lys Pro Thr Ile Lys Pro Thr Asn Lys Pro Thr Thr Lys
 65                  70                  75                  80

ACC ACC AAC AAA CGT GAT CCG AAA ACC CCG GCG AAA ATG CCG AAG AAG         288
Thr Thr Asn Lys Arg Asp Pro Lys Thr Pro Ala Lys Met Pro Lys Lys
                 85                  90                  95

GAA ATC ATC ACC AAC                                                     303
Glu Ile Ile Thr Asn
            100

(2) INFORMATION FOR SEQ ID NO:5:

(i) SEQUENCE CHARACTERISTICS:
        (A) LENGTH: 30 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:5:

Asn Asn Asp Ser His Ser Glu Val Ser Asn Ser Val Pro Ser Ser Ile
1               5                   10                  15

Cys Ser Asn Asn Pro Thr Cys Trp Ala Ile Ser Lys Arg Ile
                20                  25                  30

(2) INFORMATION FOR SEQ ID NO:6:

(i) SEQUENCE CHARACTERISTICS:
        (A) LENGTH: 30 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:6:

Asn Asn Val Pro Ser Ser Ile Cys Ser Asn Asn Pro Thr Cys Trp Ala
1               5                   10                  15

Ile Ser Lys Arg Ile Pro Asn Lys Lys Pro Gly Lys Lys Thr
                20                  25                  30

(2) INFORMATION FOR SEQ ID NO:7:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:7:

AGCTTGGCTG TTCCGCCATG GCTCGAG                                    27

(2) INFORMATION FOR SEQ ID NO:8:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:8:

CCGAATTCAA GCTTAGATGC TCTAGCAAAA GCCAAG                          36

(2) INFORMATION FOR SEQ ID NO:9:

(i) SEQUENCE CHARACTERISTICS:
        (A) LENGTH: 48 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:9:

```
                                     -continued

CCCCTGCAGT TAGGATCCCT CGAGAGGTAA TGCAGCTAAA ATTTCATC                    48

(2) INFORMATION FOR SEQ ID NO:10:

(i) SEQUENCE CHARACTERISTICS:
         (A) LENGTH: 30 base pairs
         (B) TYPE: nucleic acid
         (C) STRANDEDNESS: single
         (D) TOPOLOGY: linear (ii) MOLECULE TYPE: DNA (genomic)

(xi) SEQUENCE DESCRIPTION: SEQ ID NO:10:

CCGAATTCTC GAGGCTCCTA AAGAAAATAC                                        30

(2) INFORMATION FOR SEQ ID NO:11:

(i) SEQUENCE CHARACTERISTICS:
         (A) LENGTH: 41 base pairs
         (B) TYPE: nucleic acid
         (C) STRANDEDNESS: single
         (D) TOPOLOGY: linear (ii) MOLECULE TYPE: DNA (genomic)

(xi) SEQUENCE DESCRIPTION: SEQ ID NO:11:

CCAAGCTTGG ATCCTGCGCA GATCTTGGTG TTGGTTTTTT G                           41
```